United States Patent [19]

Florjancic

[11] Patent Number: 5,275,185
[45] Date of Patent: Jan. 4, 1994

[54] DENTURES CLEANSING DEVICE

[76] Inventor: Peter Florjancic, Isarstrasse 25, 8109 Wallgau, Fed. Rep. of Germany

[21] Appl. No.: 947,524

[22] Filed: Sep. 18, 1992

[30] Foreign Application Priority Data

Sep. 20, 1991 [DE] Fed. Rep. of Germany ....... 9111776
Dec. 10, 1991 [DE] Fed. Rep. of Germany ....... 4140575

[51] Int. Cl.$^5$ .............................................. B08B 3/04
[52] U.S. Cl. ...................................... 134/93; 134/182; 206/83
[58] Field of Search ............... 206/83, 63.5; 134/6, 134/7, 34, 93, 154, 161, 166; 433/77, 97, 167

[56] References Cited

U.S. PATENT DOCUMENTS

| | | | |
|---|---|---|---|
| 2,102,643 | 12/1937 | Pellegrini | 206/83 |
| 2,122,583 | 7/1938 | Parizot | 206/83 |
| 2,565,899 | 8/1951 | Wilcox | 206/83 |
| 2,568,838 | 9/1951 | Wilcox | 206/83 |
| 2,659,380 | 11/1953 | Jackson | 206/83 |
| 2,964,047 | 12/1960 | Jackson et al. | 206/83 |
| 2,973,767 | 3/1961 | Cohen | 206/83 |
| 3,009,468 | 11/1961 | Eberle | 206/83 |
| 4,724,855 | 2/1988 | Jackson et al. | 206/83 |
| 5,184,718 | 2/1993 | Albert | 206/83 |

Primary Examiner—Jimmy G. Foster
Attorney, Agent, or Firm—Notaro & Michalos

[57] ABSTRACT

A dentures cleaning device for receiving at least one denture and a liquid comprises a container having two oppositely positioned side walls and an outlet aperture in the container. A lid is hingedly fixed to the container for closing the container and has a filling aperture for passing the liquid into the container. A lock is provided for locking the lid to the container. A step is positioned in the container near each side wall. Also, a separation wall is positioned on one of the steps and spaced parallel away from the side wall. The separation wall is shorter than the side wall for defining an overflow space. The outlet aperture communicates with the overflow space for passing the liquid from the container; and a rib is provided on each step perpendicular to the side walls.

15 Claims, 3 Drawing Sheets

FIG. 5
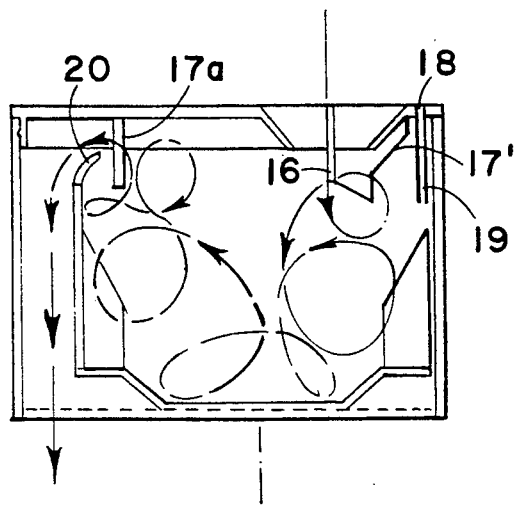
FIG. 6
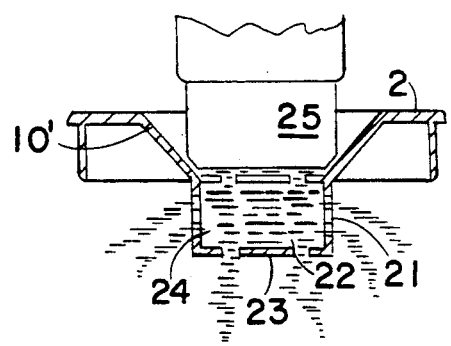
FIG. 7
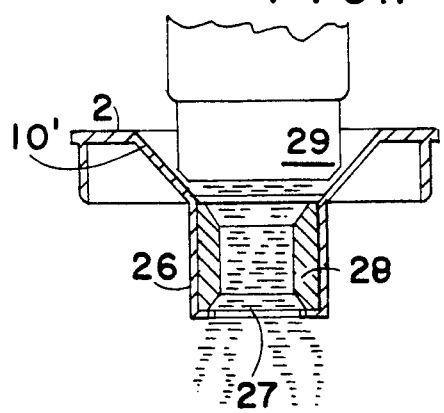
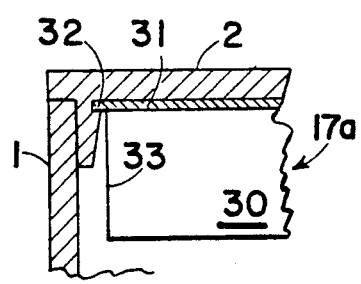
FIG. 8

DENTURES CLEANSING DEVICE

FIELD AND BACKGROUND OF THE INVENTION

Today, dentures are cleansed by cleansing tablets, cleansing powders or liquids, or by means of ultrasonic devices. All of the containers known to the Applicant that are designed for the cleansing of dentures by means of cleansing agents consist of three parts. First, of the container itself into which a cleansing tablet can be placed; second, of a screen wall or an insert with screen wall covering the table, onto which one places the dentures horizontally, one on top of the other; and third, of a loosely fitting lid.

The horizontal cross section of such a container, which usually has a circular form, is the result of the average size of the horizontally-lying dentures.

This version of the container, however, has its drawbacks, such as the denture which is placed on top of the one lying first receives only a small amount of the cleansing power of the dissolved tablet, or none at all. A further drawback is that when a container having double dentures falls on the ground, it breaks apart into five pieces so that one frequently has to search all around; and the denture can also be damaged. Besides, in many cases it would suffice to clean the denture under running water, but in order to position properly in the stream, demands a certain amount of skill and patience. Additionally, ultrasonic cleaning devices have their own drawbacks in that they are expensive and require power.

SUMMARY OF THE INVENTION

The present invention provides for a denture cleansing device that can thoroughly clean a denture consisting of two parts, in running water, in a short period of time through the use of a cleansing agent, that is easy to apply and store; and is made in one piece.

BRIEF DESCRIPTION OF THE DRAWINGS

FIG. 5 is a view of a second embodiment of FIG. 2;

FIG. 6 is a view illustrating a first embodiment of an intake funnel;

FIG. 7 is a view illustrating a second embodiment of an intake funnel; and

FIG. 8 is a partial view in cross-section of FIG. 5.

DESCRIPTION OF THE PREFERRED EMBODIMENTS

Figure 1:
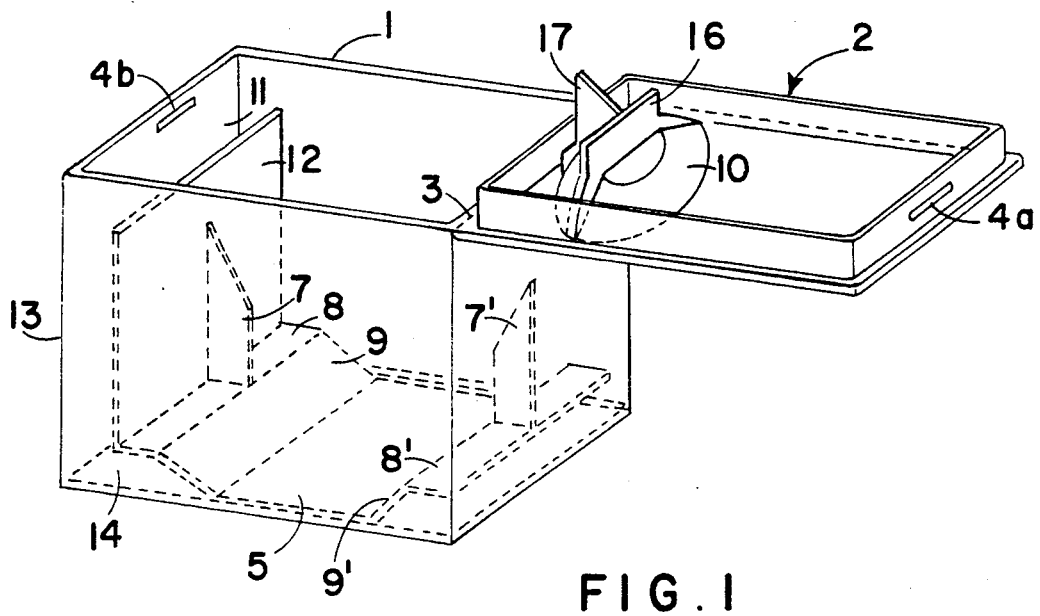
FIG. 1 is a parallel-perspective view of a cleansing device according to the present invention.

According to the present invention, as illustrated in FIG. 1, a container 1 and a lid 2 are first connected by a hinge 3, e.g. a film hinge, and can be quickly closed. A spring lock 4a, 4b firmly hold lid 2 against container 1 and ensures that the device, if dropped, does not release dentures P, P' (FIG. 4).

The container 1 has a rectangular horizontal and vertical cross section and two stages, whereby the lower stage serves as a tablet holder 5 and its shape allows tablet 6 (FIG. 3) to fall into the proper place immediately after it has been thrown into the container 1.

Figure 4:
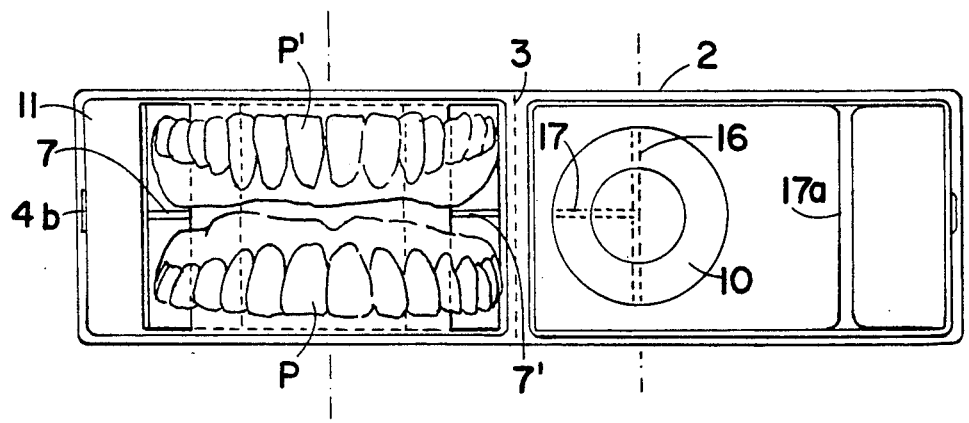
FIG. 4 is a top plan view of FIG. 3.

As shown in FIG. 4, dentures P,P' are separated by two separating ribs 7, 7' and are supported by two side steps 8, 8' (FIG. 1) so that the dentures P, P' stand vertically and side-by-side. In this way, the dentures P, P' are both seized by a whirling water jet that emerges in the container 1 and thereby cleaned. The tablet holding bottom surface 5 and the steps 8, 8' are interconnected through slanting surfaces 9, 9' as shown in FIG. 1.

Outside of the middle of the lid 2, on the side of the hinge 3, there is according to the invention, a filling funnel 10. If the container 1 is closed, it is pushed from below with the funnel 10 and the lid 2 against a water tap 25 (FIG. 6) or 29 (FIG. 7) and, in the case that the cleaning will be carried out by means of a cleansing agent 28, e.g. a dose of cleansing powder or a tablet, the container 1 has to be filled with the necessary water. The superfluous water can flow away through an overflow 11. As shown in FIG. 1, the overflow 11 comprises an inner separation wall 12 which is parallel to and spaced a short distance from a side wall 13. The separation wall 12 faces away from the filling funnel 10 and stands on the step 8 and is much shorter than the side wall 13 such that water in the container 1 can flow over its upper edge and through an opening 14 in the bottom of the container 1 and into, e.g. a sink.

The present invention allows for one to cleanse dentures without using any special cleansing agent, which considerably increases its practical value.

Figure 2:
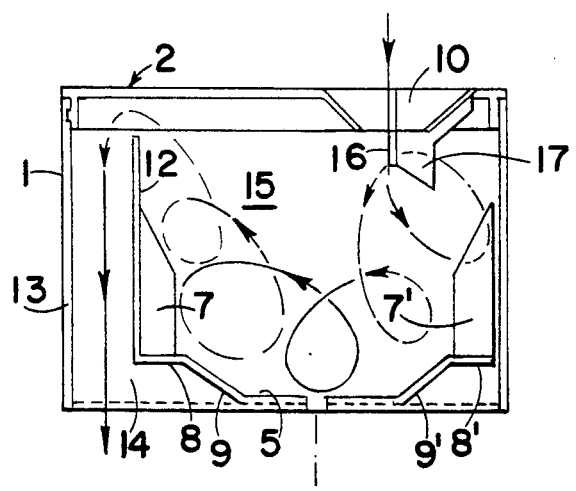
FIG. 2 is a vertical-sectional view of FIG. 1 in its closed position.

This principle of cleansing with overflowing water functions as follows. One presses the closed container 1 with the hand from below against a water tap and lets warm water flow through it. Because the container 1 has different walls, ribs and steps which act as rebound walls, and the outlet 14 is placed opposite of the inflowing water, a whirling flow appears in its intake room 15 (FIG. 2) which loosens food and washes it away through overflow and outlet 14. This is a particular advantage when the container 1 is taken on a journey. Dentures P, P' can be cleaned without other people noticing it. In addition, the present invention takes up less space than the known round-shaped cleansing containers.

Figure 3:
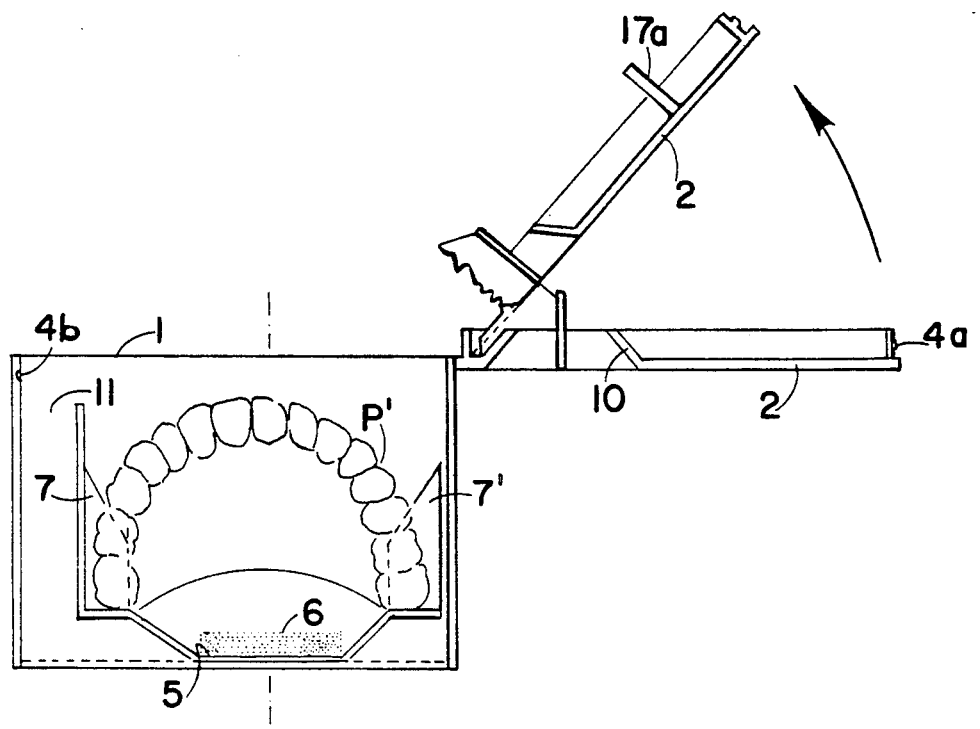
FIG. 3 is a view of FIG. 2 with an open lid.

The turbulent and whirling effect in the container can be enhanced by splitting the jet of water coming through the funnel 10. To this purpose, splitting ribs are inserted into the intake end of the funnel 10, for example, a rib 16 spanning the entire intake opening, and a rib 17 lying across and spanning only half of the intake opening. As shown in FIGS. 3, 4 and 5, a rebound wall 17a is in the lid 2, which, when the lid 2 is closed, juts out into the intake room 15 (FIG. 2) and lies apart from the separation wall 12.

As shown in FIG. 5, a hole 18 in the top is positioned near the intake funnel 10 and, continuing into a small tube 19 which reaches inside the container 1. The outer edge of the cross-lying rib 17' is shaped as a small tube 19. Through water flowing through the intake funnel 10 in the direction of the arrow, the outer air is sucked through the hole 18 and mixed via the tube 19 with the water set whereby the cleaning effect is made even stronger.

Besides the above described rebound and guiding surfaces, such as the separation wall 12, the two ribs 16 and 17, the rebound wall 17a and the slant surfaces 9, a further enhancement of the whirling is provided by other surfaces such as an inner separation wall 12 which, as shown in FIG. 5, ends in a bending 20 oriented toward the inside.

FIG. 6 illustrates another embodiment of the intake funnel 10', ending on the inner side into a sleeve 21, in which an opening 22 in a horizontal closing wall 23 and, possibly, openings 24 in the side wall of the funnel 10' divide the jet of water running from the end of the tap 25. On the other hand, another embodiment of the funnel shown at 10" in FIG. 7 has a sleeve 26 connected to the funnel 10" for receiving in its central opening 27, ring-formed tablets 28. While water runs through, such a tablet 28 slowly dissolves, mixes with the water and whirls between the dentures P, P' so that these get completely cleansed. The dirt is moved over the container's overflow 11.

Similarly, the funnel 10', as shown in FIG. 6, can be used to fill the sleeve 21 with a cleansing tablet or powder.

FIGS. 6 and 7 also illustrate that the intake funnel 10' and 10" respectively can be adapted to fit the diameters of different water taps or outlet nozzles 25 (FIG. 6) or 29 (FIG. 7).

The channel formed by overflow 11 can, together with the outlet opening 14 be used for wall hanging on an angle piece.

FIG. 8 illustrates the rebound wall 17a of FIG. 5 as a slidable wall, so that the room between this and the separation wall 12 is adjustable manually in order to decrease or increase, as the need arises, the effect of the nozzle brought about by the gap. To this purpose the rebound wall 17a' has the form of an L-piece having a longer leg 30 which constitutes the actual rebound wall, whereas both ends of a somewhat longer shorter leg 31 are inserted or pressed into lateral gaps 32 in side walls 33 of the lid 2. The lateral gaps and the leg 31 must be dimensioned so that the rebound wall can only be moved by hand and not by the water pressure.

What is claimed is:

1. A dentures cleaning device for receiving at least one denture and a liquid, the device comprising:
   a container having two oppositely positioned side walls and an outlet aperture in the container;
   a lid hingedly fixed to the container for closing the container, the lid having a filling aperture for passing the liquid into the container;
   locking means for locking the lid to the container;
   a step positioned in the container near each side wall;
   a separation wall on one of the steps and spaced parallel away from the side wall, the separation wall being shorter than the side wall, the separation wall and the side wall defining an overflow space, the outlet aperture communicating with the overflow space for passing the liquid from the container; and
   a rib on each step perpendicular to the side walls.

2. The dentures cleaning device according to claim 1, including a slant surface on each step.

3. The dentures cleaning device according to claim 2, wherein the ribs are perpendicular with the steps.

4. The dentures cleaning device according to claim 1, wherein the separation wall is positioned on an edge of the step.

5. The dentures cleaning device according to claim 1, wherein the outlet aperture is located at a bottom of the container.

6. The dentures cleaning device according to claim 1, wherein the filling aperture includes a funnel in the lid, the funnel being adaptably engageable with a water tap, the funnel also being located on a side of the lid away from the separation wall.

7. The dentures cleaning device according to claim 6, wherein the funnel includes a sleeve which extends into the container when the lid is closed.

8. The dentures cleaning device according to claim 7, wherein the sleeve includes a bottom having at least one opening in the bottom.

9. The dentures cleaning device according to claim 7, wherein the sleeve adaptably receives a cleaning tablet.

10. The dentures cleaning device according to claim 6, wherein the filling aperture further includes a first jet splitting rib spanning over the funnel.

11. The dentures cleaning device according to claim 10, wherein the filling aperture further includes a second jet splitting rib perpendicular to the first jet splitting rib.

12. The dentures cleaning device according to claim 11, wherein the second jet splitting rib comprises a tube.

13. The dentures cleaning device according to claim 6, including the lid having a hole therethrough near the funnel and a tube communicating with the hole, the tube extending into the container when the lid is closed.

14. The dentures cleaning device according to claim 1, including a rebound wall perpendicularly positioned in the lid for extending into the container when the lid is closed.

15. The dentures cleaning device according to claim 14, including the lid having lid side walls, the lid side walls having slots therein and the rebound wall having an L-shaped configuration, the rebound wall comprising a short leg slidably engageable with the slots of the side walls and a longer leg extending perpendicular to the short leg and extendable into the container when the lid is closed.

* * * * *